(12) United States Patent
Kishi et al.

(10) Patent No.: US 12,179,770 B2
(45) Date of Patent: Dec. 31, 2024

(54) ATTENTION ABILITY TEST DEVICE, ATTENTION ABILITY TEST METHOD, AND VEHICLE

(71) Applicant: TOYOTA JIDOSHA KABUSHIKI KAISHA, Toyota (JP)

(72) Inventors: Hiroshi Kishi, Toyota (JP); Kentaro Yokoi, Toyota (JP); Shinji Nakamura, Nagoya (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 192 days.

(21) Appl. No.: 17/973,875

(22) Filed: Oct. 26, 2022

(65) Prior Publication Data

US 2023/0136521 A1 May 4, 2023

(30) Foreign Application Priority Data

Oct. 28, 2021 (JP) ................................ 2021-176850

(51) Int. Cl.
*B60W 40/08* (2012.01)
*B60W 50/08* (2020.01)

(52) U.S. Cl.
CPC ............ *B60W 40/08* (2013.01); *B60W 50/08* (2013.01)

(58) Field of Classification Search
CPC .............................. B60W 40/08; B60W 50/08
USPC .......................................................... 340/576
See application file for complete search history.

(56) References Cited

U.S. PATENT DOCUMENTS

| | | | | |
|---|---|---|---|---|
| 4,028,819 A | * | 6/1977 | Walker | ................... A61B 5/165 434/258 |
| 2020/0060603 A1 | * | 2/2020 | Bower | ................... A61B 5/167 |
| 2022/0079486 A1 | * | 3/2022 | Kishi | ................... A61B 5/7475 |

FOREIGN PATENT DOCUMENTS

| | | |
|---|---|---|
| JP | 2022046987 A | 3/2022 |
| WO | WO2009075385 A1 | 6/2009 |

* cited by examiner

*Primary Examiner* — Naomi J Small
(74) *Attorney, Agent, or Firm* — Dinsmore & Shohl LLP

(57) ABSTRACT

An attention ability test device includes a display having a display area, an input device for receiving an operation performed by an examinee, and a test controller. While displaying a central image in the central area of the display area and displaying one or more peripheral images in the peripheral area of the display area, the test controller generates at random at least one of a center task of changing the central image and a periphery task of changing the peripheral image, and measures, as a reaction time, the period of time from generation of the center task or the periphery task to execution of a predetermined operation performed by the examinee having recognized the generation, and evaluates the attention ability of the examinee, based on the reaction time.

10 Claims, 14 Drawing Sheets

ATTENTION ABILITY TEST DEVICE, ATTENTION ABILITY TEST METHOD, AND VEHICLE

CROSS REFERENCE TO RELATED APPLICATION

This application claims priority to Japanese Patent Application No. 2021-176850 filed on Oct. 28, 2021, which is incorporated herein by reference in its entirety including the description, claims, drawings, and abstract.

TECHNICAL FIELD

This specification discloses an attention ability test device and an attention ability test method for testing the attention ability of an examinee, and a vehicle equipped with the attention ability test device.

BACKGROUND

Information processing ability which one can demonstrate to accomplish a target task (for example, a task of driving a vehicle) varies depending on one's visual attention ability. In driving an automobile, in particular, ninety percentage of the information utilized is said to be visual information. The level of visual attention ability is thus very important in accomplishing a task of driving an automobile.

Such a visual attention ability (hereinafter referred to as an "attention ability") varies largely depending on one's inherent characteristics, whether or not alcohol has been drunk, the extent of awareness, the content of a task being simultaneously performed, or the like. In particular, a spatial attention ability does not remain constant, and is known to generally be largest in central vision and decrease sharply from the central vision to the peripheral vision.

In recent years, a technique for testing an attention ability, or an attention ability testing technique, for accurately testing the state of such an attention ability has been demanded. The attention ability testing technique is usable to determine, for example, whether an examinee has drunk alcohol. That is, as drinking alcohol generally causes a significant decrease in attention ability, compared with not drinking, testing the attention ability of an examinee makes it possible to determine whether the examinee has drunk alcohol prior to the test. In addition, such an attention ability test device is usable when granting a driver's license to determine whether an examinee is capable of a driving task. Further, an attention ability test device is usable in a test for examining change in attention ability due to diseases, lack of sleep, medicines, aging, or the like, not limited to drinking. Despite such a demand, no such a technique for accurately testing the attention ability of examinees has conventionally been available.

International Publication 2009/075385 discloses a visual field examining apparatus that sequentially displays three kinds of examination marks at respective predetermined display positions around a center fixation mark displayed at a predetermined position on a display screen, to see whether a subject can visually recognize the respective examination marks displayed around the center fixation mark while staring at the center fixation mark, to thereby inspect the visual field of the subject. This apparatus, however, merely examines the visual field of a subject, but not an attention ability. Further, the apparatus cannot detect the subject averting their eyes from the center fixation mark, and continues examining the visual field even when the subject is not appropriately staring at the center fixation mark. Consequently, an attention ability within a visual field and a nearby area cannot be appropriately measured.

In view of the above, this specification discloses an attention ability test device and an attention ability test method for more accurately testing the attention ability of an examinee, and a vehicle equipped with such an attention ability test device.

SUMMARY

According to one aspect of this specification, there is provided an attention ability test device including: a display having a display area; an input device for receiving an operation performed by an examinee; and a test controller, wherein the test controller generates at random at least one of a center task and a periphery task while displaying a central image in the central area of the display area and one or more peripheral images in the peripheral area of the display area, the center task being a task of changing the central image, the periphery task being a task of changing the peripheral image, then measures, as a reaction time, the period of time from the generation of the center task or the periphery task to execution of a predetermined operation by the examinee having recognized the generation, and evaluates the state of the attention ability of the examinee, based on the reaction time.

As a center task and a periphery task are both executed, it is possible to individually evaluate the attention ability in the central vision of an examinee and that in the peripheral vision of an examinee. This enables more accurate testing of the attention ability of an examinee. In addition, the periphery task and the center task are both a "changing task" in which an image changes, and are more difficult than an "appearing task" in which an image appears. Setting a higher level of difficulty for the periphery task enables accurate testing of the attention ability in the peripheral vision even when the display area is small, in other words, when a peripheral image cannot be displayed at a position sufficiently separated from the central image.

In an embodiment, the test controller may display a plurality of peripheral images in the peripheral area, and execute a periphery task of changing one peripheral image selected at random from among the plurality of peripheral images.

Use of a plurality of peripheral images further enhances the level of difficulty of the periphery task. This enables accurate testing of the attention ability in the peripheral vision even when the display area is small, that is, when a peripheral image cannot be displayed at a position sufficiently separated from the central image.

In an embodiment, the test controller may generate a center task and a periphery task at a plurality of times in a single flow of the processing for the test to obtain a plurality of center reaction times and a plurality of periphery reaction times, the center reaction time being a reaction time relative to the center task, the periphery reaction time being a reaction time relative to the periphery task, and the test controller may calculate a center evaluation value indicating the attention ability of the examinee in the central vision, based on the plurality of center reaction times, and a periphery evaluation value indicating the attention ability of the examinee in the peripheral vision, based on the plurality of periphery reaction times.

Executing a center task and a periphery task at a plurality of times enables more accurate testing of the attention ability. In addition, individual calculation of a center evaluation value and a periphery evaluation value enables individual evaluation of the attention ability of the examinee in the central vision and that in the peripheral vision.

In an embodiment, the center evaluation value may be the sum of a representative value of the plurality of center reaction times and an excessive sample variation of the center reaction time, the periphery evaluation value may be the sum of a representative value of the plurality of periphery reaction times and an excessive sample variation of the periphery reaction time, and the excessive sample variation may be the root mean square of the deviation between the representative value and one or more excessive samples among the plurality of reaction times, the excessive sample being a reaction time larger than the representative value.

An examinee who has been drinking will find difficulty in keeping a high attention ability, and the attention ability will drop sharply as time passes or in response to a disturbance. As an excessive sample variation is a value remarkably reflecting such a sharp drop in the attention ability, use of a value obtained by adding the excessive sample variation to the representative value as an evaluation value enables a more accurate determination of whether or not an examinee has been drinking alcohol.

In an embodiment, the test controller may generate a memorizing task in the central area of the display area in parallel with a center task or a periphery task. The memorizing task may be to present a target image as a memorizing target to the examinee, and then sequentially display a plurality of candidate images, including the target image, in a random order as memorizing task images in the central area, and the test controller may count, as a number of correct answers, the number of times that the examinee, having recognized the display of the target image as the memorizing task image in the central area, executes a predetermined operation within a predetermined permissible time after the display.

Executing a memorizing task in parallel with a center task and a periphery task can enhance the respective levels of difficulty of the center task and the periphery task. This makes it possible to maintain a level of difficulty of a center task and that of a periphery task, suitable for a test of an attention ability, which enables more accurate testing of the attention ability. In addition, as a center task is generated in the central area, an examinee always has their eyes, or line of sight, directed to the central area. This makes the examinee more readily keep their eyes in a condition suitable for the test, which enables more accurate testing of the attention ability.

In an embodiment, the test controller may calculate the evaluation value of the memorizing task, based on the number of correct answers, and the test controller may determine the need of a retest in a case where the evaluation value of the memorizing task is less than a predetermined memorizing threshold.

A low evaluation value of a memorizing task suggests a possibility that the examinee did not have their eyes directed to the central area during the processing for the test, which leads to a low reliability of the test. In such a case, the need of a retest is determined in order to improve the reliability of the result of a test conducted using the attention ability test device.

In an embodiment, the display may be a vehicle-mounted display mounted in a position where the display area is visually recognizable from the driver's seat, and the input device may include one or more steering switches equipped on the steering wheel of the vehicle.

This structure facilitates execution of a test of attention ability of a driver.

According to another aspect of this specification, there is provided a vehicle including the attention ability test device described above, and a vehicle controller for controlling the behavior of the vehicle, wherein the vehicle controller changes the behavior of the vehicle, based on the result of evaluation outputted from the attention ability test device.

The behavior of the vehicle is changed based on the result of evaluation outputted from the attention ability test device, so that the safety of the vehicle can be further enhanced.

According to another aspect of this specification, there is provided an attention ability test method including the steps of generating at random at least one of a center task and a periphery task while displaying a central image in the central area of the display area of a display and one or more peripheral images in the peripheral area of the display area, the center task being a task of changing the central image, the periphery task being a task of changing the peripheral image, then measuring, as a reaction time, the period of time from the generation of the center task or the periphery task to execution of a predetermined operation by an examinee having recognized the generation, and evaluating the state of the attention ability of the examinee, based on the reaction time.

As a center task and a periphery task are both executed, it is possible to individually evaluate the attention ability in the central vision of an examinee and that in a peripheral vision. This enables more accurate testing of the attention ability of the examinee. Moreover, the periphery task and the center task are both set as a "changing task" in which an image changes, which is more difficult than an "appearing task" in which an image appears. Setting a higher difficulty of a periphery task enables accurate testing of the attention ability in a peripheral vision even when the display area is small, in other words, when a peripheral image cannot be displayed at a position sufficiently separated from the central image.

The technique disclosed in this specification enables more accurate testing of the attention ability of an examinee.

BRIEF DESCRIPTION OF DRAWINGS

Embodiment(s) of the present disclosure will be described based on the following figures, wherein.

DESCRIPTION OF EMBODIMENTS

Figure 1:
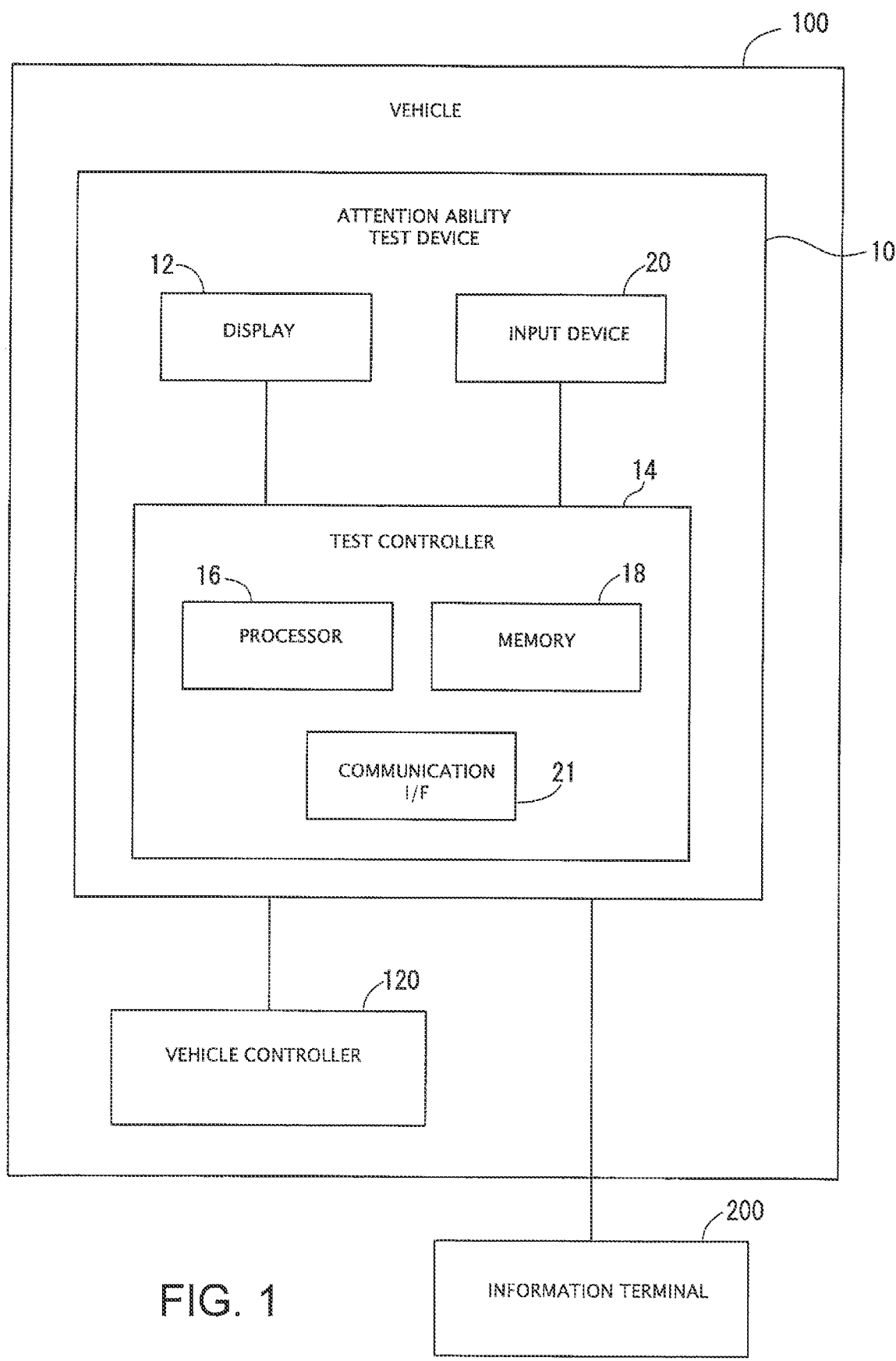
FIG. 1 is a block diagram of the structure of a vehicle equipped with an attention ability test device.
Figure 2:
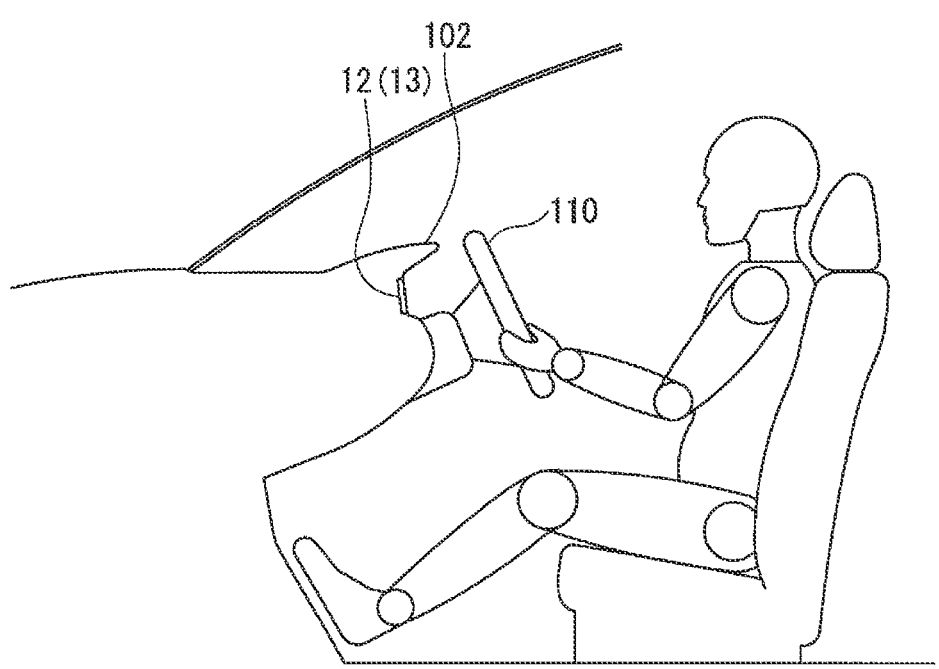
FIG. 2 is a schematic view of an area around the driver's seat of a vehicle.
Figure 3:
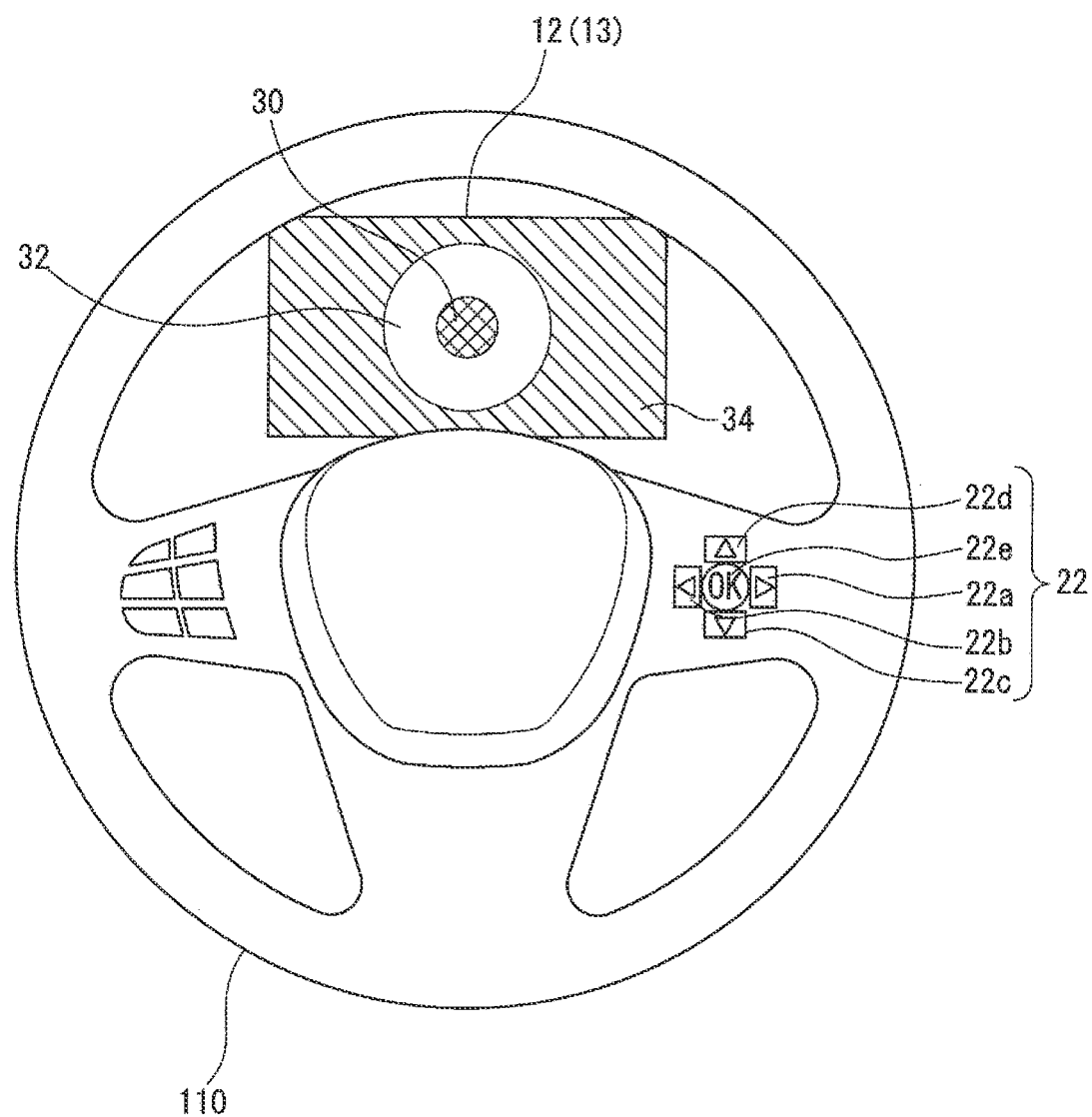
FIG. 3 illustrates one exemplary field of view of a driver.

With reference to the accompanying drawings, an attention ability test device 10 and a vehicle 100 equipped with the attention ability test device 10 will now be described. FIG. 1 is a block diagram of the structure of a vehicle 100 equipped with the attention ability test device 10. FIG. 2 is a schematic view of an area around the driver's seat of the vehicle 100. FIG. 3 illustrates one exemplary field of view of a driver.

The attention ability test device 10 is a device for testing the visual attention ability of an examinee. The attention ability test device 10 in this example is mounted in a vehicle 100, and tests the attention ability of a driver, who is an examinee. Note here that a person's attention ability largely varies, depending on their condition on the day, such as the amount of alcohol consumed, sleeping hours, the extent of nervousness, the presence/absence of disease, or the like, in addition to their inherent characteristics. In other words, one's attention ability varies every day. The attention ability test device 10 in this example is used to test the attention ability of a driver, which varies every day, to determine the presence/absence of abnormality on the driver, in particular, whether or not they have been drinking.

As illustrated in FIG. 1, the attention ability test device 10 includes a display 12, an input device 20, and a test controller 14. The display 12 is, for example, a liquid crystal display, an organic electroluminescent (EL) display, a projector, or the like, and displays an image for testing an attention ability. Specifically, the display 12 has a display area 13 positioned such that a driver on the driver's seat can see the display area 13. In this example, a meter display is used as the display 12 of the attention ability test device 10. A meter display is a display 12 installed in the instrument panel 102 of the vehicle 100, and generally displays information such as the running speed or the fuel level of the vehicle 100. The display 12, or a meter display, is located on the opposite side from the driver relative to the steering wheel 110, as illustrated in FIG. 3.

Note that although a meter display is used as the display 12 in this example, the display 12 may have any other structure. That is, the display 12 may not be a meter display, and the display screen of a navigation device may be used as the display 12. Alternatively, in the case of a vehicle having a head-up display for displaying an image in the air ahead of a transparent reflection panel (for example, a windshield glass, or the like), the head-up display may be used as the display 12 of the attention ability test device 10. Still alternatively, a dedicated display 12 may be installed so as to function as an attention ability test device 10, rather than using an extant display equipped to the vehicle 100. Still alternatively, the display of a portable information terminal, such as a smart phone, carried in the vehicle 100 may be used as the display 12 of the attention ability test device 10.

Figure 4:
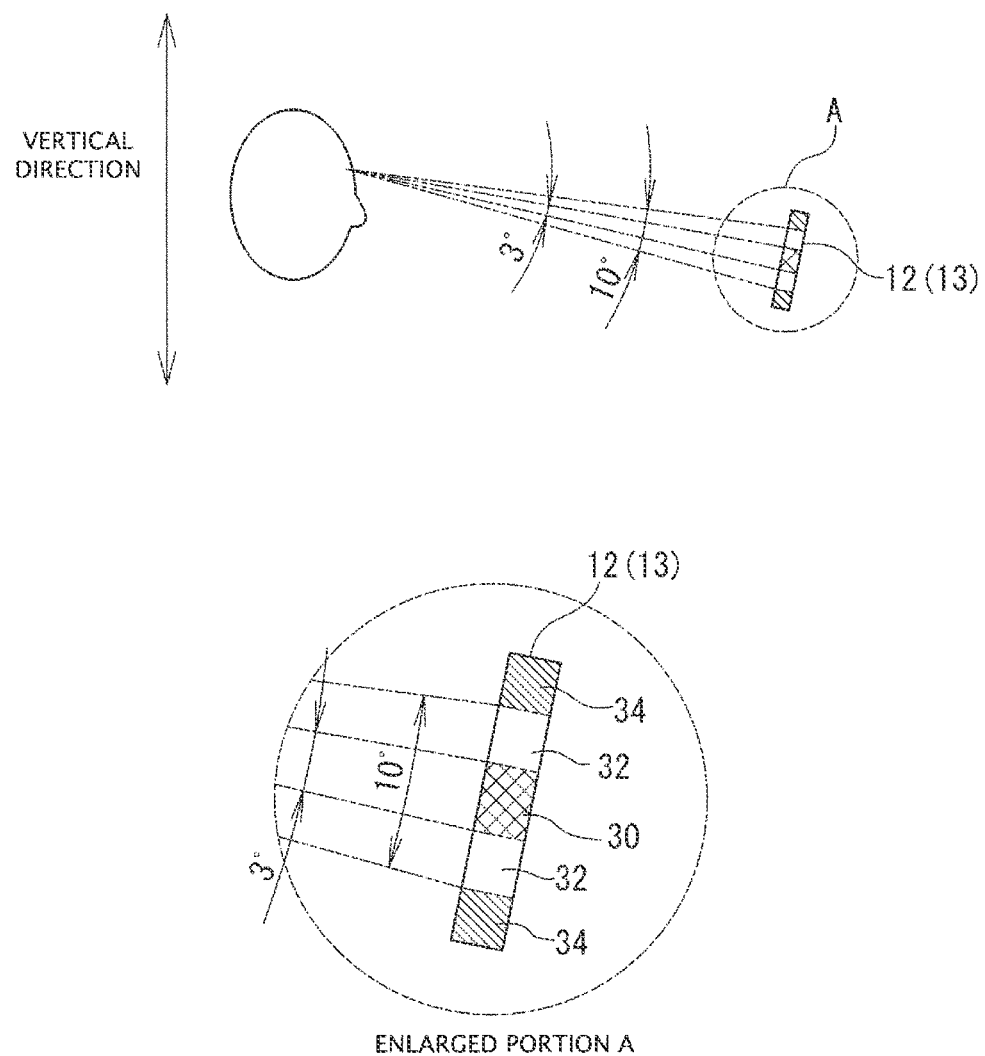
FIG. 4 explains the ranges of a central area and a peripheral area.

In this example, the display area 13 of the display 12 is divided into three sections, namely, a central area 30, a peripheral area 34, and an intermediate area 32, as will be described referring to FIGS. 3 and 4. FIG. 4 is a schematic view to describe the dividing of the display area 13. In FIGS. 3 and 4, an area with cross-hatching in the display area 13 represents the central area 30, an area with diagonal lines represents the peripheral area 34, and an area without hatching represents the intermediate area 32.

The central area 30 is an area located at the center of the display area 13 that will be captured on the fovea of a human eye. As illustrated in FIG. 4, the central area 30 has a dimension corresponding to three degrees or less of a visual field. The peripheral area 34 is an area more outward than the central area 30, specifically, being an area more outward than ten degrees of a visual field, as illustrated in FIG. 4. Note that the position and dimension of the peripheral area 34 may be arbitrarily modified depending on the distance between the driver and the display area 13 or the dimension of the display area 13, or the like.

The input device 20 receives an operation inputted by a driver, or an examinee. In this example, a steering switch 22 (refer to FIG. 3) provided on the steering wheel 110 is used as the input device 20. The form of the input device 20 is arbitrarily modified. For example, any other extant device equipped in the vehicle 100 may be used as the input device 20. Alternatively, a switch or a keyboard dedicated to the attention ability test device 10 may be provided for use as the input device 20. In the case of a touch panel display 12, a touch sensor for detecting a touch operation may be used as the input device 20. Alternatively, an audio input device for detecting an utterance by an examinee as an inputted operation may be used as the input device 20.

The test controller 14 controls driving of the display 12, and executes the processing for testing an attention ability, which will be described later. The test controller 14 sends the result of a test to a vehicle controller 120 or an information terminal 200 outside the vehicle when necessary. Such a test controller 14 is physically a computer having a processor 16, a memory 18, and a communication interface 21 (hereinafter referred to as a communication I/F), as illustrated in FIG. 1. The "computer" includes a microcontroller including a computer system integrated in a single integrated circuit. The processor 16 refers to a processor in a broader sense, and includes a general-purpose processor (for example, a Central Processing Unit (CPU)) or a dedicated processor (for example, a Graphics Processing Unit (GPU), an Application Specific Integrated Circuit (ASIC), a Field Programmable Gate Array (FPGA), a programmable logical device, or the like). The memory 18 may include at least one of a semiconductor memory (for example, a Random Access Memory (RAM), a Read Only Memory (ROM), a solid state drive, or the like) and a magnetic disk (for example, a hard disk drive or the like). The communication I/F 21 sends and receives data with respect to the vehicle controller 120 or an information terminal 200 outside the vehicle. Although the test controller 14 and the vehicle controller 120 are separate entities in FIG. 1, the vehicle controller 120 may be used as the test controller 14.

Figure 5:
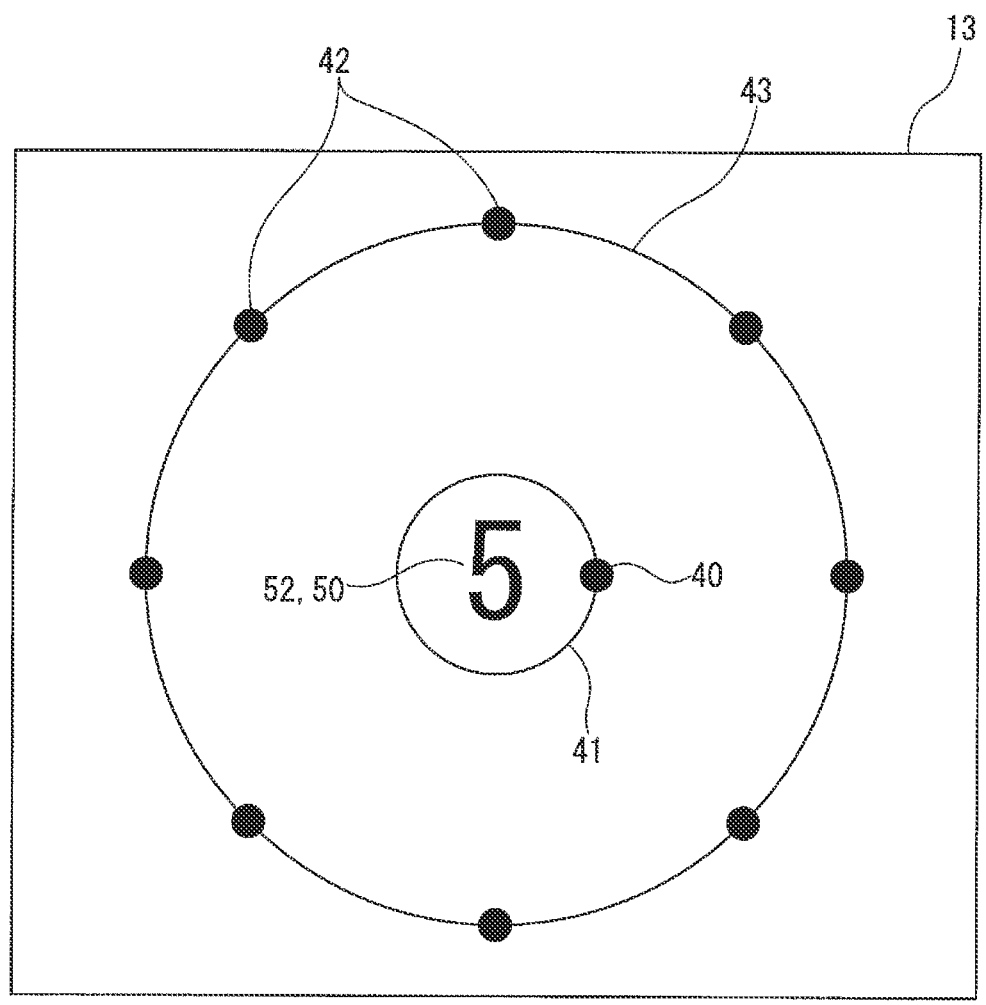
FIG. 5 illustrates one exemplary screen displayed in a display area when testing an attention ability.
Figure 6:
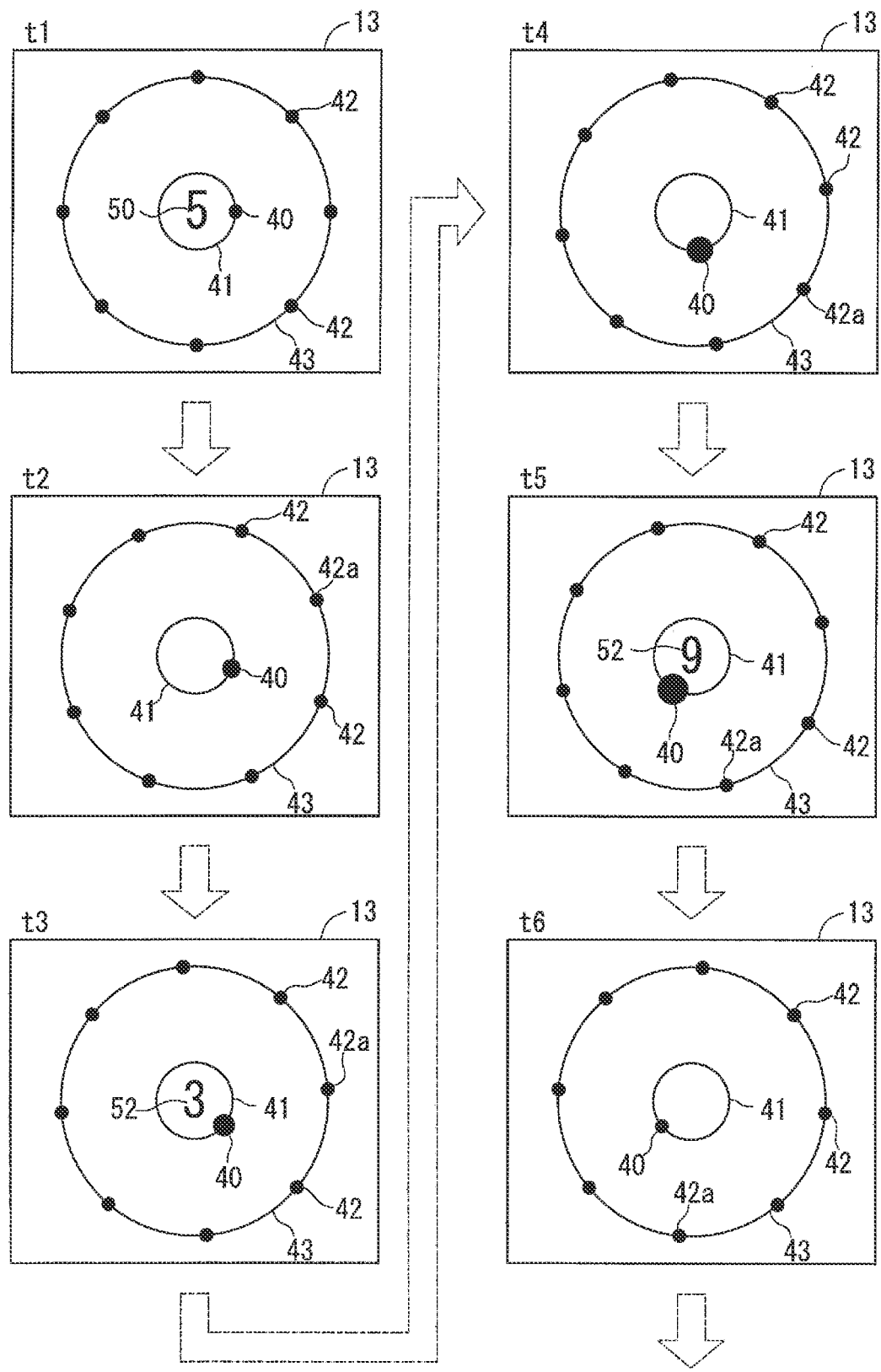
FIG. 6 illustrates screens that are sequentially displayed in a display area when testing an attention ability.
Figure 7:
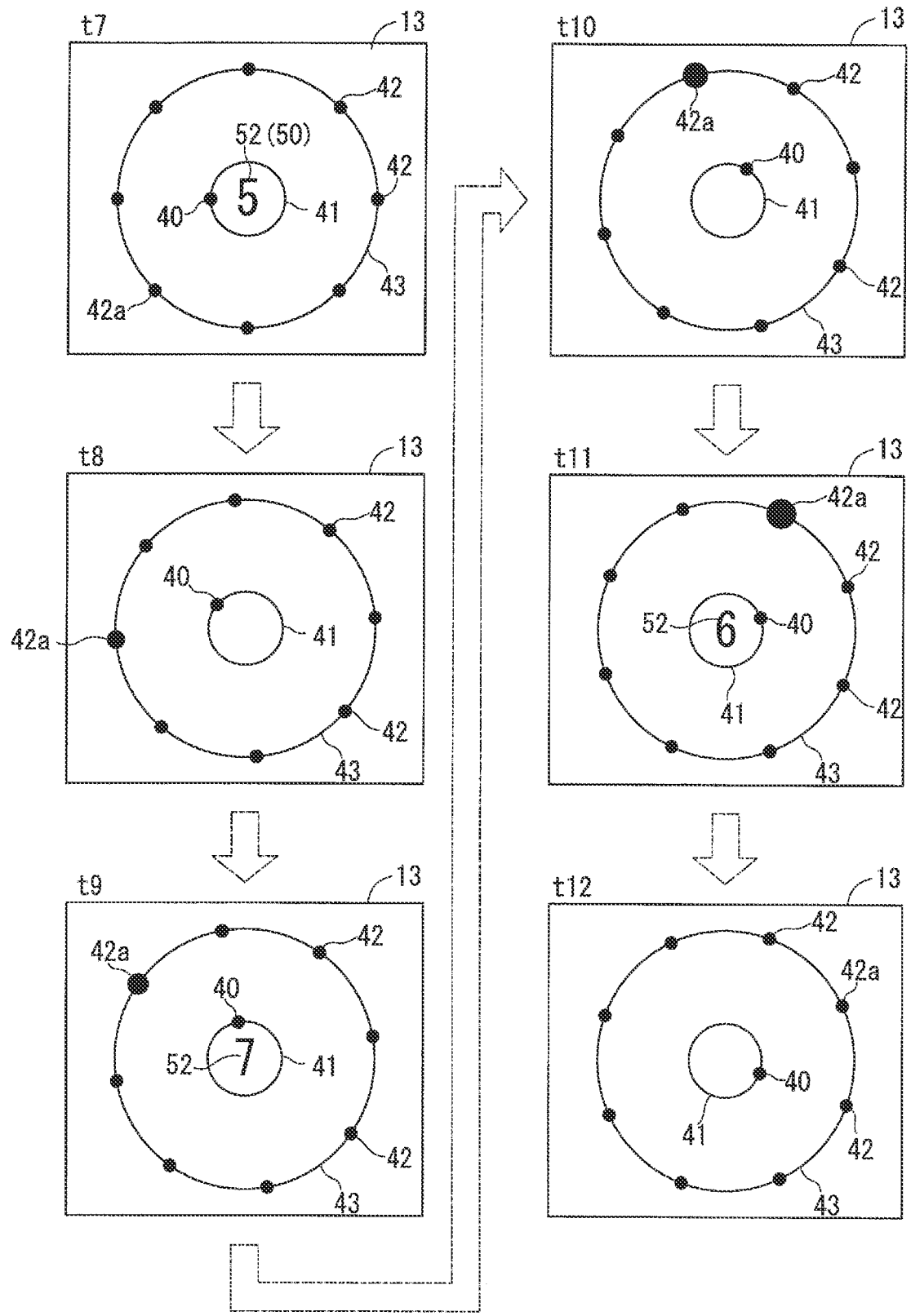
FIG. 7 illustrates screens that are sequentially displayed in a display area when testing an attention ability.

Referring to FIGS. 5 to 7, the content of a test to be executed by the attention ability test device 10 will now be described. FIG. 5 illustrates an exemplary screen to be displayed in the display area 13 when testing an attention ability. FIGS. 6 and 7 illustrate screens to be sequentially displayed in the display area 13.

As illustrated in FIG. 5, when testing an attention ability, a central image 40 and a peripheral image 42 are displayed in the display area 13. The central image 40 is a figure to be displayed in the central area 30 (the reference numeral not shown in FIG. 5) of the display area 13. The central image 40 moves circularly at a constant speed during the processing of the test. In this example, the central image 40 is a small black circle. In the central area 30, a route image 41, or a large circle, representing a route along which the central image 40 moves is also displayed.

A peripheral image 42 is a figure to be displayed in the peripheral area 34 (not shown in FIG. 5) of the display area 13. As illustrated in FIG. 5, the peripheral image 42 is a small black circle, the same as the central image 40. In the peripheral area 34, a plurality of peripheral images 42 are displayed aligned at constant intervals in the circumferential direction, as illustrated in FIG. 5. The plurality of peripheral images 42 move circularly at a constant speed. In the peripheral area 34, a route image 43, or a large circle, representing a route along which the peripheral image 42 moves is also displayed.

With the central image 40 and peripheral image 42 displayed, the test controller 14 presents a center task, a periphery task, and a memorizing task to an examinee. A center task is a task for testing the attention ability in the central vision of an examinee. In this example, a center task is to change the central image 40 at a constant changing speed.

In the example in FIGS. 6 and 7, a center task is generated during the period from time t1 to time t5. As illustrated in FIG. 6, with a center task generated, the central image 40 changes at a constant changing speed while moving along the circular route image 41. More specifically, with a center task generated, the central image 40 expands at a constant expanding speed. An examinee, having recognized the change of the central image 40, executes a predetermined operation correlated to the center task. A predetermined operation which an examinee should execute upon recognition of generation of a center task will be hereinafter referred to as a "center reaction operation". In this example, a center reaction operation is to press a switch (for example, a rightward switch 22a) correlated to the center task among a plurality of steering switches 22 of the input device 20. The test controller 14 measures the period of time after generation of the center task, that is, after the central image 40 starts changing, until execution of the center reaction operation, as a center reaction time C[i]. In the example in FIG. 6, the period of time from time t1 to time t5 constitutes the center reaction time C[i].

A periphery task is a task for testing an attention ability in the peripheral vision of an examinee. In this example, a periphery task is to change one peripheral image 42 selected at random from among a plurality of peripheral images 42 at a constant changing speed. In the example in FIGS. 6 and 7, a periphery task is generated during the period from time t7 to t11. As illustrated in FIG. 7 or as described above, a plurality of peripheral images 42 move along the large circle of the route image 43 at a constant speed. With a periphery task generated, any one peripheral image 42a of the plurality of peripheral images 42 changes at a constant changing speed while moving. More specifically, the peripheral image 42a expands at a constant expanding speed. An examinee, having recognized the change of the peripheral image 42, executes a predetermined operation correlated to the periphery task. A predetermined operation which an examinee should execute upon recognition of generation of a periphery task will be hereinafter referred to as a "periphery reaction operation". In this example, a periphery reaction operation is to press a switch (for example, a leftward switch 22b) correlated to the periphery task among the plurality of steering switches 22 of the input device 20. The test controller 14 measures the period of time after generation of a periphery task, that is, after the peripheral image 42 starts changing, until execution of a periphery reaction operation, as a periphery reaction time P[i]. In the example in FIG. 7, the period of time from time t7 to time t11 constitutes a periphery reaction time P[i].

In a test of an attention ability, a center task and a periphery task are generated at random at a plurality of times, but not simultaneously. Specifically, during a period with a center task generated, that is, during a period with the central image 40 changing at a constant speed, the peripheral image 42 does not change but keeps moving at a constant speed. Meanwhile, during a period with the peripheral image 42 changing at a constant speed, the central image 40 does not change but keeps moving at a constant speed. In the case where a center reaction operation or a periphery reaction operation is executed, the test controller 14 causes the central image 40 and the peripheral image 42 to return to the state before the change, that is, the state before expansion. For example, in the example in FIG. 6, as a center reaction operation is executed at time t5, the central image 40 is in a state before expansion at time t6.

As is obvious from the above description, a center task, which is generated in the central area 30, and a periphery task, which is generated in the peripheral area 34, are generated at random in this example. This enables testing of both an attention ability in the central vision of an examinee and that in the peripheral vision. As a result, the condition, that is, whether high or low, of the attention ability of an examinee, in particular, the presence/absence of an attention ability suitable for driving, can be accurately determined.

Note here that although the central image 40 and the peripheral image 42 are both a small black circle in the above-described example, the central image 40 and the peripheral image 42 can be arbitrarily modified. For example, the central image 40 may have any shape, for example, a polygon, a character, or an illustration, such as a food or an animal, not limited to a circle. Further, the central image 40 may be colored in any color provided that the color is readily distinguishable from the background color. Similarly, the peripheral image 42 may have any other shape, not limited to a circle, and be colored with any color, not limited to black. Although the central image 40 and the peripheral image 42 have the same shape in this example, the central image 40 and the peripheral image 42 may have different shapes from each other. For example, the central image 40 may be a circle, while the peripheral image 42 may be a cross mark. The number of peripheral images 42 may be arbitrarily changed to any number equal to two or greater.

Although the peripheral image 42 expands in the above-mentioned example, the central image 40 may change in any other manner in a center task, not limited to any particular change, provided that the change is non-circulative. Specifically, a change in a center task may be a change in dimension, color, brightness, moving speed, or shape of the central image 40, or any combination of these. Further, a center task may change the color of the central image 40 from black to red or the shape of the central image 40 from circle to rhomboid. Further, a center task may be to expand the central image 40 while increasing the brightness of the central image 40. Note that a "non-circulative change" refers to a change in which the state before the change has started is not restored even after elapse of time, unless a center reaction operation is executed or a time is over. A "non-circulative change" does not include a periodical blinking or circulating motion of the peripheral image 42.

Similarly, change of the peripheral image 42 in a periphery task may be any non-circulative change, beside expansion. Change of the central image 40 caused in a center task and change of the peripheral image 42 caused in a periphery task may be different from each other. For example, the central image 40 may expand in a center task, and the peripheral image 42 may change its shape in a periphery task.

As is obvious from the above description, a center task and a periphery task are both a "changing task" in which an image changes in this example. This structure ensures an appropriate level of difficulty. That is, the attention ability test device 10 in this example is used to determine the presence/absence of driver abnormality, in particular, whether or not the driver has been drinking. Determination of the presence/absence of such an abnormality requires the center task and the periphery task to be executed in the test to have an appropriate level of difficulty. In other words, an excessively low difficulty may enable an examinee to achieve a good performance equivalent to that which is achieved in a normal state (for example, when not drinking) even though the examinee is in an abnormal state (for example, when having drunk). This hinders determination as to the presence/absence of abnormality, based on the performance in the task. Meanwhile, an excessively high difficulty may lower the performance of an examinee in the task even when the examinee is in a normal state. This also hinders determination as to the presence/absence of abnormality, based on the performance in the task. That is, appropriate determination of the presence/absence of abnormality requires the task to have an appropriate level of difficulty.

It is assumed here that the peripheral image 42 is displayed at a position sufficiently separated from where the central image 40 is displayed. This enlarges an area to which an examinee needs to pay attention, which increases the difficulty of the task. The attention ability test device 10 in this example, however, is to be mounted in the vehicle 100, which makes it difficult to ensure a sufficiently large display area 13, and thus to display the peripheral image 42 at a position sufficiently separated from the display area 13. To address the above, the center task and the periphery task are both set as a "changing task" in this example. With a "changing task" in which an image changes it is more difficult to find a change, compared with an "appearing task" in which an image appears or a "vanishing task" in which an image vanishes. In view of the above, setting both the center task and the periphery task as a "changing task" can ensure an appropriate level of difficulty despite the small dimension of the display area 13, which enables appropriate testing of an attention ability.

Moreover, a plurality of peripheral images 42 are displayed and any one of the plurality of peripheral images 42 is caused to change in a periphery task in this example. This structure ensures an appropriate level of difficulty despite the small dimension of the display area 13. That is, in this example, the display area 13 is small in dimension, and it is thus difficult to display the peripheral image 42 in a position sufficiently separated from the central image 40, as described above. In a case where the peripheral image 42 cannot be displayed at a position sufficiently separated from the central image 40 and there is only one peripheral image 42 displayed, an examinee can relatively readily find the change of the peripheral image 42. This hinders appropriate testing of the attention ability of the examinee. In contrast, in a case where a plurality of peripheral images 42 are displayed, as is in this example, an examinee is required to pay attention to one central image 40 and the plurality of peripheral images 42 all the time. This can enhance the level of difficulty of the test to an appropriate level despite the small dimension of the display area 13.

A memorizing task will now be described. A memorizing task is a task to be generated in parallel with a center task and a periphery task. In a memorizing task, a specific image is presented as a target image to an examinee so that the examinee memorizes the specific image. Then, a plurality of candidate images, including the target image, are displayed one by one at random in the central area 30 of the display area 13. The examinee then executes a predetermined operation correlated to the memorizing task when an image that is the same as the target image they have memorized is displayed. Note that a predetermined operation which an examinee should execute upon recognition of display of a target image will be hereinafter referred to as a "memorizing reaction operation". In this example, a memorizing reaction operation is to press a switch correlated to a memorizing task (for example, an OK switch 22e) among the plurality of steering switches 22 of the input device 20.

Such a memorizing task will be more specifically described. The test controller 14 has a plurality of candidate images stored in advance in the memory 18 for use in a memorizing task. Although images of numbers from one to nine are used as candidate images in this example, the candidate images can be any other images, not limited to the images of numbers, provided that the images share a common theme. For example, images of letters, images of a plurality of kinds of polygons, images of illustrations of a plurality of kinds of fruits, and so forth, may be used as candidate images.

The test controller 14 selects any one candidate image as a target image from among the plurality of candidate images, and displays the selected target image in the central area 30 for only a predetermined memorizing period. A memorizing period is, for example, as long as about a few seconds. An examinee memorizes the displayed image as a target image. In the example in FIGS. 6 and 7, the image of number "5" is displayed as a target image 50 for only a memorizing period that starts at time t1.

After elapse of the memorizing period, the test controller 14 selects images one by one at random from a plurality of candidate images including the target image 50 as a memorizing task image 52, and displays in the central area 30. Specifically, in the example in FIGS. 6 and 7, the image of number "3" is displayed as a memorizing task image 52 at time t3, and the image of number "9" is displayed as the memorizing task image 52 at time t5. Note that the memorizing task images 52 may be displayed sequentially or at an interval, that is, with a blank period without display after the end of display of one memorizing task image 52 before the start of display of an immediately following memorizing task image 52. Such a blank period may be as long as or longer than a period for displaying one memorizing task image 52.

Thereafter, the image of number "5" is again displayed as the memorizing task image 52 at time t7 in the example in FIGS. 6 and 7. As the image of number "5" is a target image 50 in the example in FIGS. 6 and 7, the test controller 14 monitors whether the examinee executes a memorizing reaction operation within a predetermined permissible period Tm after time t7, or a time when the target image 50 is displayed as the memorizing task image 52. Note that a permissible period Tm is not limited to any particular period, and can be as long as a few seconds, for example. In general, a permissible period Tm is shorter than the period of time after the end of display of one memorizing task image 52 before the start of display of an immediately following memorizing task image 52 in order to clearly determine that a reaction operation is made with respect to a particular image.

As a memorizing task is generated in the central area 30 in parallel with a center task and a periphery task, as described above, an examinee always has their eyes, or line of sight, directed to the center of the display area 13. This enables more accurate testing of the attention ability of the examinee. That is, although a test of an attention ability, using a center task and a periphery task, assumes that an examinee keeps their eyes directed to the center or an area close to the center of the display area 13, an examinee could keep staring at the central image 40 or the peripheral image 42, rather than the center of the display area 13, without a memorizing task such as is described above. In such a case, it may not be possible to accurately test the attention ability of the examinee. In contrast, with a memorizing task generated at the center of the display area 13, an examinee needs to keep their eyes directed to the center of the display area 13 all the time, which enables accurate testing of the attention ability of the examinee, using a center task and a periphery task.

Moreover, generation of a memorizing task enables increase in the level of difficulty of the center task and the periphery task despite the small dimension of the display area 13, and thus enables accurate testing of the attention ability of an examinee. In other words, as the display 12 in this example is a vehicle-mounted display, it is difficult to ensure a large display area 13, and further, as a large display area 13 is not available, it is difficult to display the peripheral image 42 in a position sufficiently separated from the central image 40. Provided that the peripheral image 42 is displayed in a position near the central image 40, an examinee can relatively readily pay attention to both the peripheral image 42 and the central image 40. As a result, it is generally difficult to increase the level of difficulty of a center task and a periphery task to an appropriately high level, using a display 12 having a small display area 13.

In this example, however, generation of a memorizing task in parallel with a center task and a periphery task causes a need for an examinee to conduct information processing in their brain all the time by comparing the memorized target image 50 with the memorizing task image 52 displayed in the central area 30. Execution of a center task and a periphery task in parallel with this information processing increases the level of difficulty of the center task and the periphery task to an appropriately high level. This enables appropriate testing of the attention ability of an examinee.

The flow of the processing for testing an attention ability, using the attention ability test device 10 will now be described. In a single flow of the proceeding for the test, a center test set and a periphery test set are repetitively executed at a plurality of times in parallel with a memorizing test set. Note that a center test set and a periphery test set each refer to processing from generation of a center task or a periphery task once to reception of an operation correlated to the task or time-out. A memorizing test set refers to processing of repetitively displaying the memorizing task image 52 after displaying the target image 50. The ratio of the effective number of times of execution between a center test set and a periphery test set in a single flow of the processing for the test is approximately three to one. That is, the effective number of times of execution of the center test set is larger than that of the periphery test set.

Figure 8:
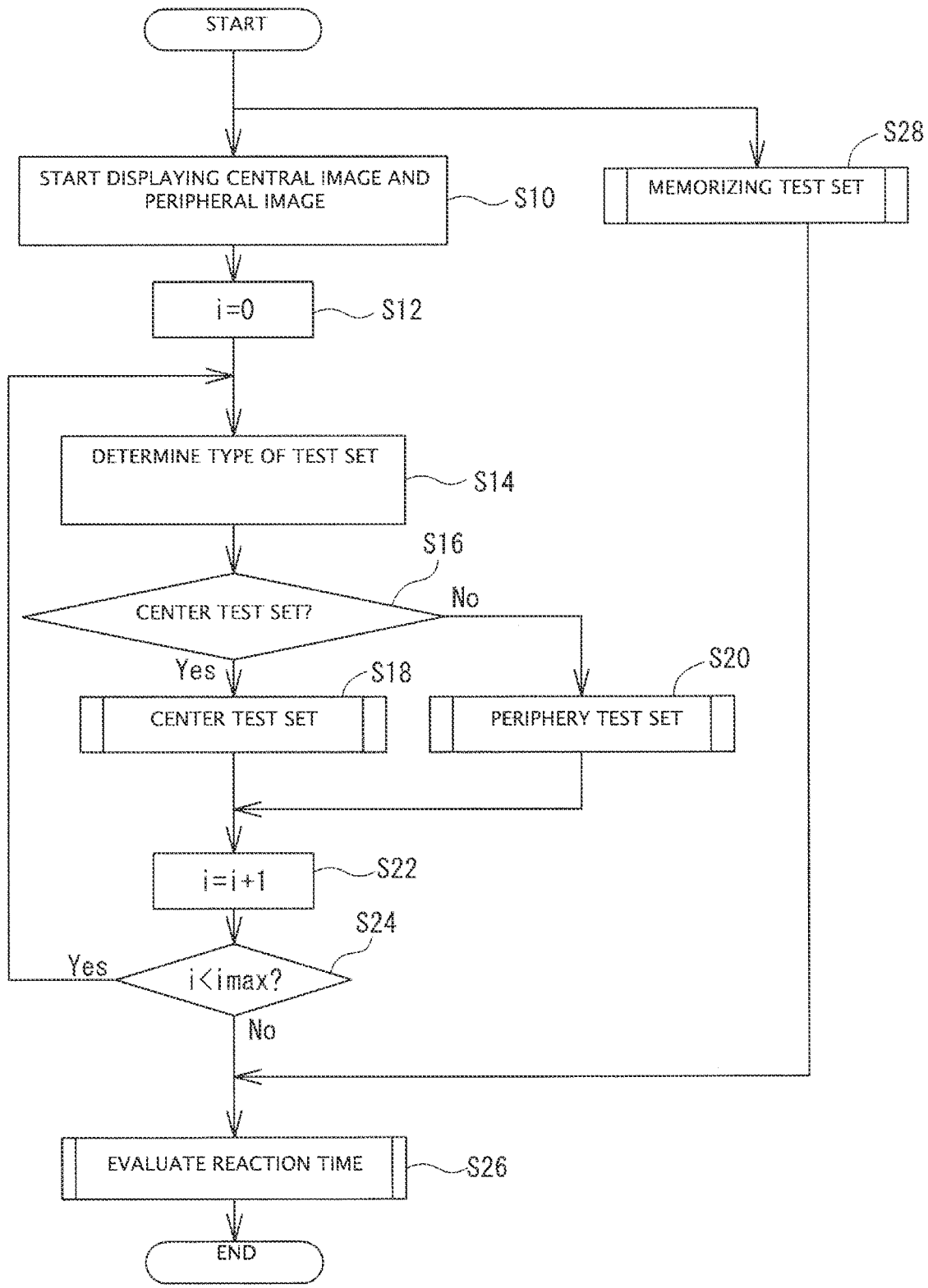
FIG. 8 is a flowchart of processing for testing an attention ability.

FIG. 8 to FIG. 13 are a flowchart of the processing for a test to be conducted with the attention ability test device 10. As illustrated in FIG. 8, in order to test an attention ability, the test controller 14 initially displays a central image 40 in the central area 30 of the display area 13 and a plurality of peripheral images 42 in the peripheral area 34 (S10). In parallel with displaying the central image 40 and the peripheral image 42, a memorizing test set is executed (S28). A specific flow of the processing for the memorizing test set will be described later.

The test controller 14 will repetitively execute a center test set and a periphery test set in parallel with a memorizing test set. Specifically, the test controller 14 initializes the number of tests i to set i=0 (S12).

Then, the test controller 14 selects at random a test set to be executed next from a center test set and a periphery test set (S14). In a case where a center test set is selected (Yes in S16), the test controller 14 executes the center test set (S18). Meanwhile, in a case where a periphery test set is selected (No in S16), the test controller 14 executes the periphery test set (S20). Respective specific flows of the processing for the center test set and for the periphery test set will be described later.

After a center test set or a periphery test set is executed once, the test controller 14 increments the number of tests i (S22), and then compares the incremented number of tests i with a predetermined necessary number of tests imax (S24). When the comparison shows i<imax (Yes in S24), the flow returns to step S14 to determine the type of a test set to be executed next and it is then determined to execute the test set. Meanwhile, in a case where the number of tests i reaches the necessary number of tests imax (No in S24), the test controller 14 evaluates the obtained center reaction time C[i] and periphery reaction time P[i] (S26). This ends the processing for the test. Note that the processing for evaluation of a reaction time will be described later in detail.

The result of evaluation obtained in step S26 may be presented to the examinee. Alternatively, the result of evaluation may be provided to the vehicle controller 120. In this case, the vehicle controller 120 may change the behavior of the vehicle 100, depending on the result of evaluation. For example, in a case where the evaluation indicates a low attention ability of an examinee (that is, a driver) and thus suggests a high possibility that the examinee has been drinking, the vehicle controller 120 may ban the vehicle 100 from running. Alternatively, the vehicle controller 120 may change the content of assistance to driving to be executed by the vehicle controller 120, depending on the result of evaluation. For example, in the case of a vehicle equipped with a brake assist function, or a known driving assist function, for automatically braking upon detection of an obstacle ahead of the vehicle 100, when the test of an attention ability shows a lower attention ability of an examinee (that is, a driver) than that at a standard level, the vehicle controller 120 may start a braking operation using the brake assist function earlier than normal.

Still alternatively, the result of evaluation may be notified to the information terminal 200 outside the vehicle so that a third party outside the vehicle can know the result of evaluation. For example, the attention ability test device 10 in this example may be mounted in a corporate vehicle owned by a corporation, and the result of a test undertaken by a driver of the corporate vehicle may be sent to an information terminal in the management division of the cooperation. In this case, a person in charge of the condition of the driver can know the condition of the driver, based on the result of evaluation sent from the attention ability test device 10 to the information terminal. Should any problem be found with the result of evaluation, the person in charge may check the condition of the driver or ban the driver from driving the vehicle.

Figure 9:
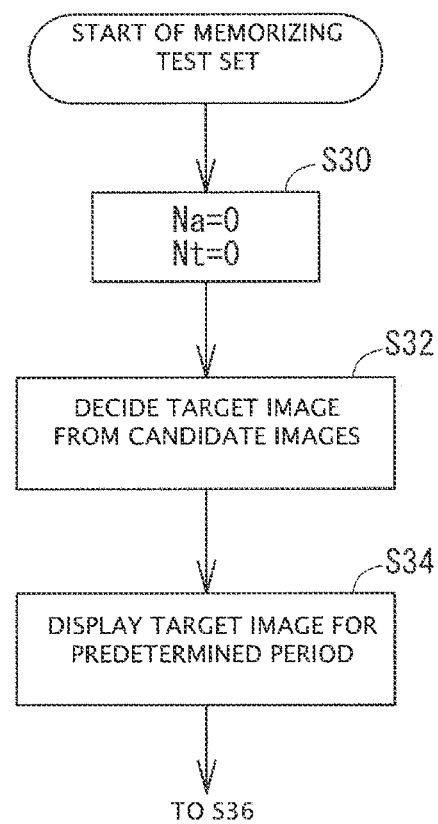
FIG. 9 is a flowchart of a first half of processing for a memorizing test set.
Figure 10:
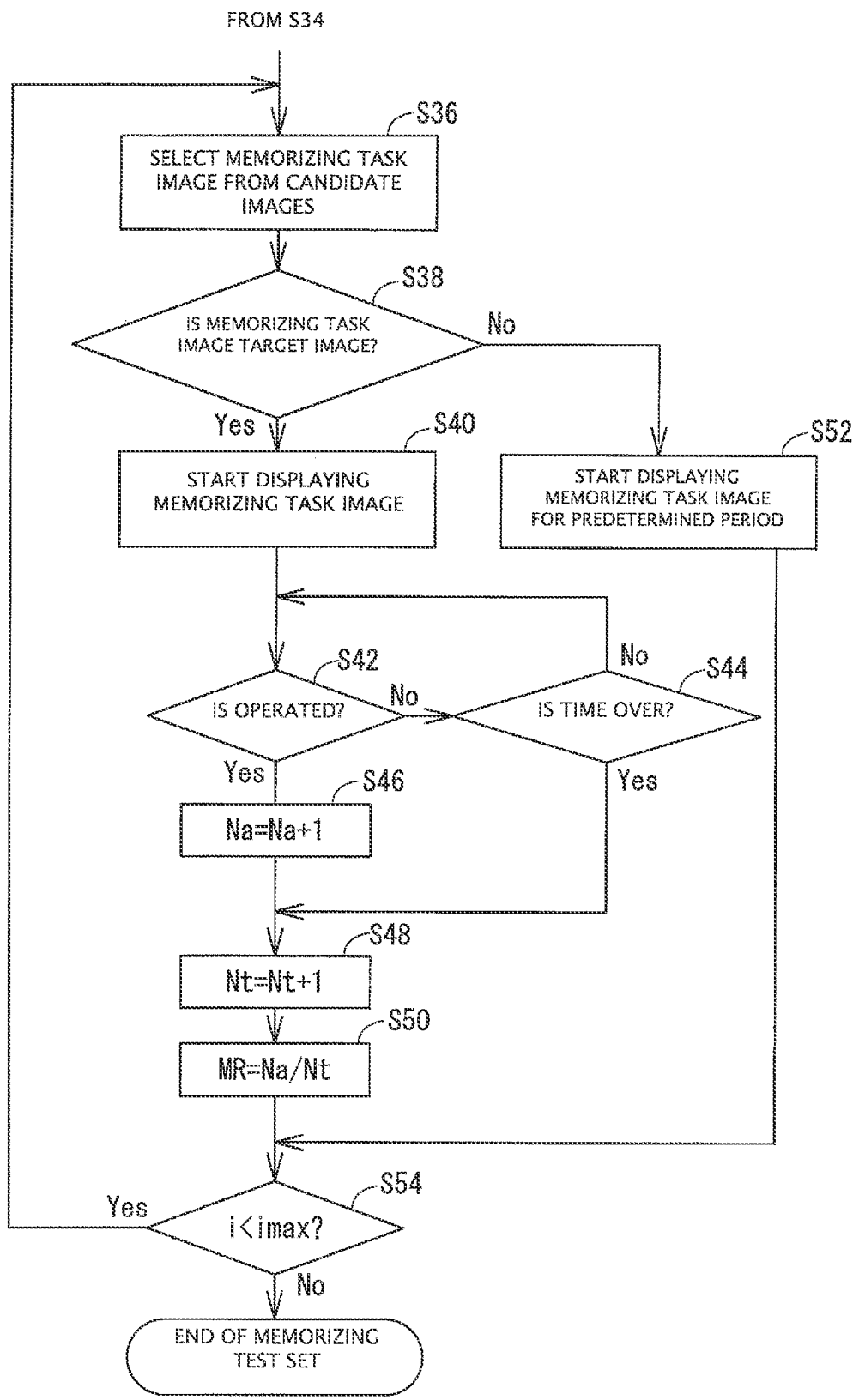
FIG. 10 is a flowchart of a second half of the processing for a memorizing test set.

Referring to FIGS. 9 and 10, the flow of the processing for a memorizing test set will now be described in detail. In executing a memorizing test set, initially, the test controller 14 initializes two parameters to be used in the memorizing test set, namely, the number of correct answers Na and a target number of times of display Nt, to set Na=0 and Nt=0 (S30). Thereafter, the test controller 14 selects one image as a target image 50 from among a plurality of candidate images (S32), and then displays the selected target image 50 at the center of the display area 13 for only a predetermined memorizing period (S34). The examinee then temporarily memorizes the displayed target image 50.

After elapse of the memorizing period, the test controller 14 selects at random one of the plurality of candidate images as a memorizing task image 52 (S36). In a case where the selected memorizing task image 52 is not the target image 50 (No in S38), the test controller 14 displays the selected memorizing task image 52 in the central area 30 for a predetermined period of time (S52).

On the other hand, in a case where the selected memorizing task image 52 is the target image 50 (Yes in S38), the test controller 14 starts displaying the memorizing task image 52 (that is, the target image 50) (S40), and then monitors whether the examinee executes a memorizing reaction operation by the time a predetermined permissible period Tm has elapsed (S42, S44). In a case where a memorizing reaction operation is executed within the permissible period Tm (Yes in S42), the test controller 14 increments the number of correct answers Na (S46), and also increments the target number of times of display Nt (S48).

On the other hand, in a case where no memorizing reaction operation is executed within the permissible period Tm (Yes in S44), the test controller 14 does not increment the number of correct answers Na but increments only the target number of times of display Nt (S48). Further, whether a memorizing reaction operation is executed, the test controller 14 calculates the rate of the number of correct answers Na relative to the target number of times of display Nt, that is, the percentage of the correct answers, as of the present moment, as a memorizing evaluation value MR (S50). The test controller 14 repeats display of the memorizing task image 52 and counting of the parameters Na, Nt, until the number of tests i reaches the predetermined necessary number of tests imax (S54).

Figure 11:
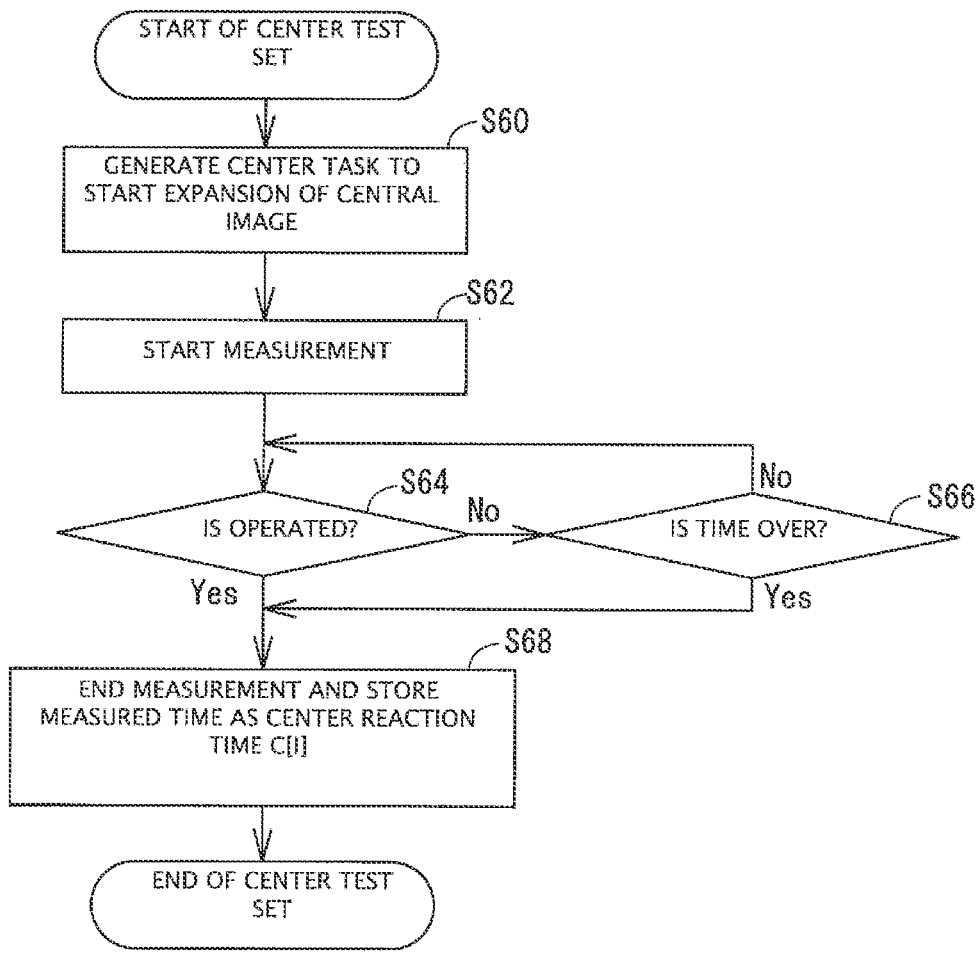
FIG. 11 is a flowchart of processing for a center test set.

Referring to FIG. 11, the flow of the processing for a center test set will now be described. As illustrated in FIG. 11, with a center test set selected, the test controller 14 generates a center task (S60). Specifically, the test controller 14 expands the central image 40 at a constant speed. In addition, the test controller 14 stars measuring the elapsed time simultaneously with the start of the expansion (S62). Note that a time when a center task is started is arbitrarily changed.

After generation of the center task, the test controller 14 monitors whether the examinee executes a center reaction operation (S64). With a center reaction operation executed (Yes in S64), the test controller 14 stops measuring the elapsed time, and stores the measured time as a center reaction time C[i] in the memory 18 (S68). Note that in a case where a switch not correlated to either of the center task or the memorizing task is pressed, that reaction operation is disregarded. Alternatively, in a case where a switch not correlated to either of the center task or the memorizing task is pressed, the flow may return to step S14, or to a step in which the type of a test set is determined, to resume the test set from the start.

On the other hand, in a case where the examinee does not execute a center reaction operation before elapse of a predetermined maximum waiting time, that is, in a case where the time is over (Yes in S66), the test controller 14 advances the flow to step S68, in which the measured time up to the present moment, or the maximum waiting time, is stored as a center reaction time C[i] in the memory 18. Note that in a case where the time is over, the flow may return to step S14, rather than step S68, to resume the test set from the start.

Figure 12:
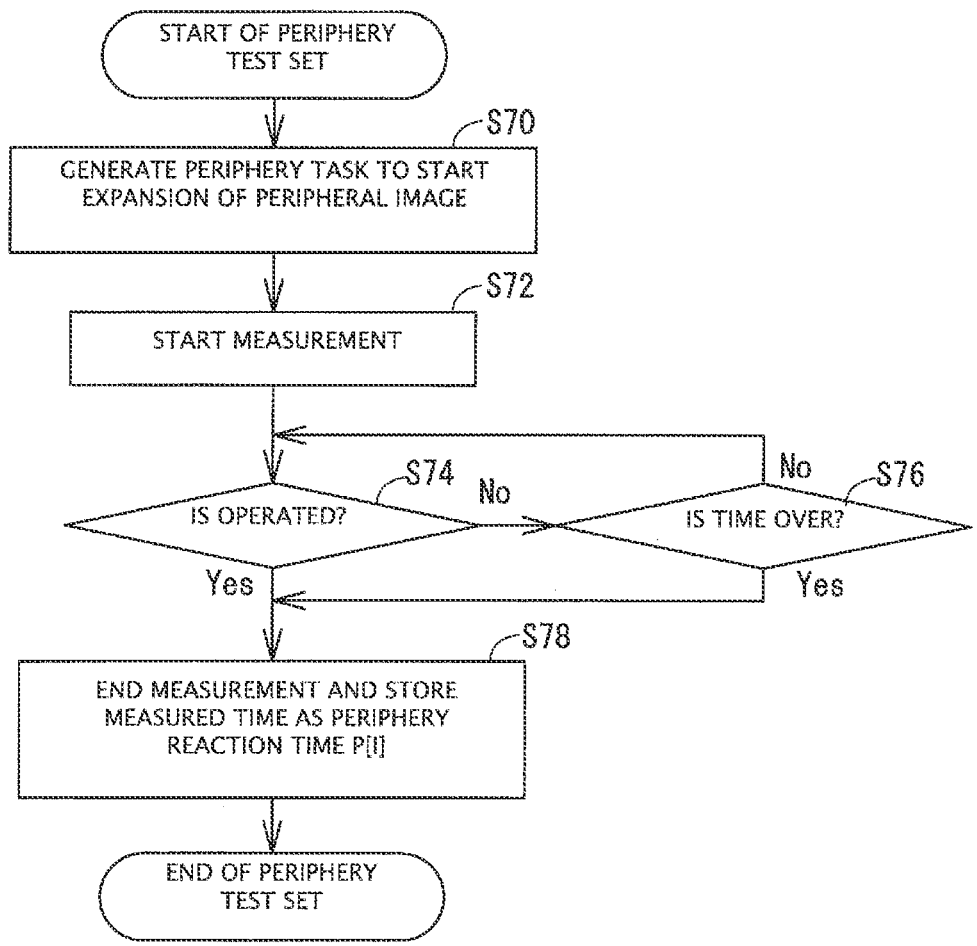
FIG. 12 is a flowchart of processing for a periphery test set.

Referring to FIG. 12, the flow of the processing for a periphery test set will now be described. As illustrated in FIG. 12, with a periphery test set selected, the test controller 14 generates a periphery task (S70). That is, the test controller 14 expands any one peripheral image 42 among the plurality of peripheral images 42 at a constant speed. In addition, the test controller 14 starts measuring the elapsed time simultaneously with the start of the expansion (S72). Note that a time when a periphery task is started is arbitrarily changed.

After generation of a periphery task, the test controller 14 monitors whether the examinee executes a periphery reaction operation (S74). With a periphery reaction operation executed (Yes in S74), the test controller 14 stops measuring the elapsed time, and stores the measured time as a periphery reaction time P[i] in the memory 18 (S78). Note that in a case where a switch not correlated to either the periphery task or the memorizing task is pressed, that reaction operation is disregarded. Alternatively, in a case where a switch not correlated to either of the periphery task or the memorizing task is pressed, the flow may return to step S14, or to a step in which the type of a test set is determined, to resume the test set from the start.

On the other hand, in a case where the examinee does not execute a periphery reaction operation before elapse of a predetermined maximum waiting time, that is, in the case that the time is over (Yes in S76), the test controller 14 advances the flow to step S78, in which the measured time up to the present moment, that is, the maximum waiting time, is stored as a periphery reaction time P[i] in the memory 18. Note that in a case where the time is over, the flow returns to step S14, rather than step S78, to resume the test set from the start.

Figure 13:
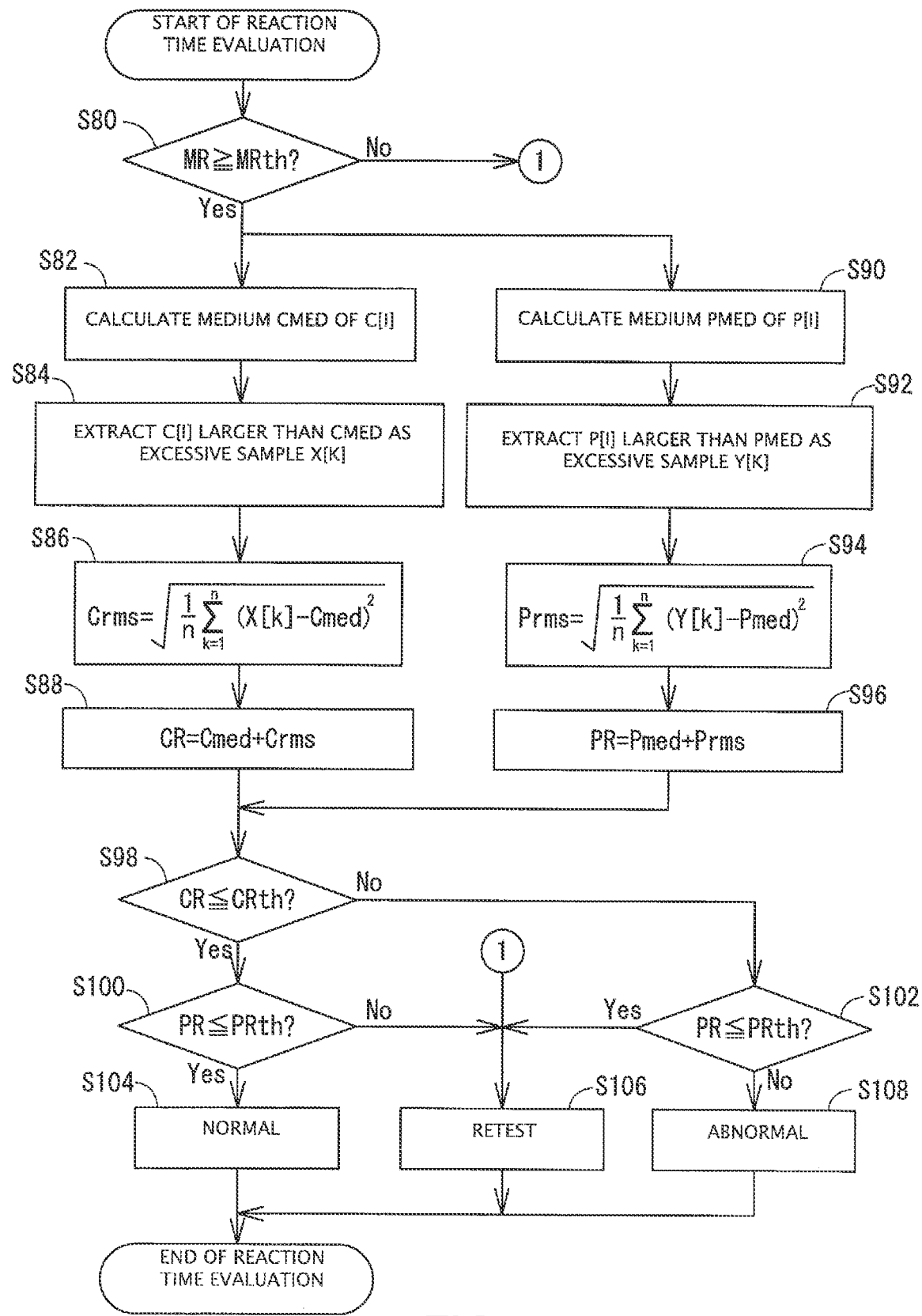
FIG. 13 is a flowchart of processing for evaluation of a reaction time.

Referring to FIG. 13, the processing for evaluation of a reaction time will now be described. In evaluation of a center reaction time C[i] and a periphery reaction time P[i], the test controller 14 initially compares the memorizing evaluation value MR with a predetermined memorizing threshold MRth (S80). The memorizing evaluation value MR is a rate of the number of correct answers Na relative to the number of times of display Nt of the target image 50 in a memorizing task, as described above, that is, the percentage of the correct answers relative to all memorizing tasks generated. A memorizing threshold MRth is the percentage of correct answers which a person having a standard level of attention ability is naturally expected to obtain. In the case that the memorizing evaluation value MR is lower than the memorizing threshold MRth (No in S80), the test controller 14 determines low reliability of the test and thus determines the need to execute the test again, or a retest (S106).

The need for a retest is determined with MR<MRth, as described above, for the reasons below. That is, as repetitively described above, accurate testing of the attention ability in the central vision of an examinee and that in the peripheral vision requires the examinee to have their eyes directed to the central area 30 of the display area 13 in this example. If the examinee stares at the peripheral area 34, rather than the central area 30, of the display area 13, the obtained periphery reaction time P[i] does not properly reflect the attention ability in the peripheral vision but reflects the attention ability in the central vision.

In view of the above, in order to cause an examinee to direct their eyes to the central area 30, a memorizing task is generated in the central area 30 in this example. A low evaluation value MR of the memorizing task means that the examinee has highly likely not had their eyes directed to the central area 30 during the test. In this case, the center reaction time C[i] and the periphery reaction time P[i] obtained in the test are of poor reliability. Accordingly, the need for a retest is determined in a case where MR<MRth results in this example.

On the other hand, in a case of MR>=MRth, the test controller 14 calculates the evaluation value CR of the center reaction time C[i] (S82 to S88) and the evaluation value PR of the periphery reaction time P[i] (S90 to S96). In calculation of a center evaluation value CR, the test controller 14 calculates the median Cmed of a plurality of center reaction times C[i] obtained in a plurality of respective test sets (S82). Then, center reaction times C[i] larger than the calculated median Cmed among the plurality of center reaction times C[i] are extracted as excessive samples X[k] (S84).

Thereafter, the test controller 14 obtains a root mean square of the deviation between the obtained median Cmed and the excessive sample X[k] (S86). That is, the median Cmed and the excessive sample X[k] are substituted into Expression 1. Expression 1 can be rewritten as an expression for calculating a value indicating the variation of excessive samples X[k] relative to the median Cmed. In the following, Crms obtained with Expression 1 will be referred to as an "excessive sample variation".

[Expression 1]

$$Crms = \sqrt{\frac{1}{n}\sum_{k=1}^{n}(X[k]-Cmed)^2}$$ Expression 1

With an excessive sample variation Crms obtained, the test controller 14 calculates the sum of the excessive sample variation Crms and the median Cmed as a center evaluation value CR (S88), namely, CR=Cmed+Crms.

Calculation of a center evaluation value CR will now be described referring to a specific example. For example, provided that seven center reaction times C[i], namely, 1.2 sec, 1.3 sec, 1.4 sec, 1.52 sec, 1.55 sec, 1.7 sec, and 18 sec, are obtained in a single flow of the test. In this case, a median Cmed=1.52 sec is obtained. Then, values larger than the median Cmed, namely, 1.55 sec, 1.7 sec, 18 sec, are extracted as excessive samples X[k].

The median Cmed=1.52 sec and the excessive samples X[k]=(1.55 sec, 1.7 sec, 18 sec) are substituted into Expression 1 to obtain an excessive sample variation Crms≈0.193. Then, a center evaluation value CR is obtained as CR=1.52+0.193=1.713.

Similar to the center evaluation value CR, the test controller 14 calculates a periphery evaluation value PR as well. The procedure for calculating a periphery evaluation value PR is the same as that for the center evaluation value CR. That is, the median Pmed of the plurality of periphery reaction times P[i] is obtained (S90), and a periphery reaction time [i] larger than the obtained median Pmed is extracted as an excessive sample Y[k] (S92). Then, the median Pmed and the excessive sample Y[k] are substituted into Expression 2 to calculate a variation of excessive samples Y[k] relative to the median Pmed, that is, an excessive sample variation Prms (S94). The obtained excessive sample variation Prms is added to the median Pmed to thereby obtain a periphery evaluation value PR (S96).

[Expression 2]

$$Prms = \sqrt{\frac{1}{n}\sum_{k=1}^{n}(Y[k]-Pmed)^2}$$ Expression 2

With the center evaluation value CR and the periphery evaluation value PR obtained, the test controller 14 compares the center evaluation value CR and the periphery evaluation value PR with a center threshold CRth and a periphery threshold PRth, respectively (S98 to S102). Note here that the center threshold CRth and the periphery threshold PRth are respective reference values that are generally set in advance to respective evaluation values CR, PR which a person having an attention ability at an appropriate level is naturally expected to obtain.

The center threshold CRth and the periphery threshold PRth can be determined in experiments conducted in advance in accordance with the purpose of the test. For example, in a case where the presence/absence of drinking alcohol is a particular subject that it is desired to determine with the attention ability test device 10, a plurality of examinees are requested to undertake the test under both conditions, namely, under a drinking condition and a non-drinking condition, to obtain evaluation values CR, PR in tests under the respective conditions. Then, a center threshold CRth and a periphery threshold PRth are determined, based on the obtained results.

Figure 14:
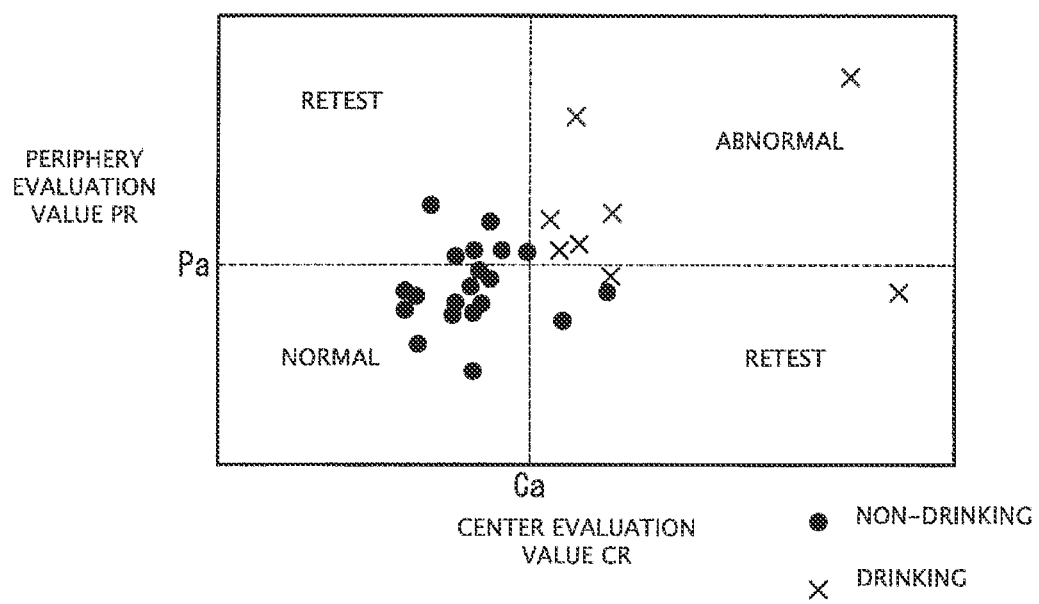
FIG. 14 illustrates exemplary results of attention ability tests under a drinking condition and a non-drinking condition, respectively.

FIG. 14 illustrates a distribution of the evaluation values CR, PR obtained in the above-described experiments, wherein the abscissa represents the center evaluation values CR, and the ordinate represents the periphery evaluation values PR. In FIG. 14, a black circle represents an evaluation value obtained with a non-drinker examinee, while a cross mark represents an evaluation value obtained with a drinker examinee. In the case illustrated in FIG. 14, most of the center evaluation values CR of non-drinker examinees are lower than the value Ca, and those of drinker examines are higher than the value Ca. Further, most of the periphery evaluation values PR of non-drinkers are lower than the value Pa, and most of those of drinkers are higher than the value Pa. Thus, with the results of experiments illustrated in FIG. 14 obtained, setting the value Ca to the center threshold CRth and the value Pa to the periphery threshold PRth enables determination, in a test, as to the presence/absence of drinking, that is, whether the driver has drunk alcohol prior to the test.

Referring to FIG. 13 again, the description of the flow of the processing for evaluation is resumed. In a case where the respective comparisons between the evaluation values CR, PR with the thresholds CRth, PRth show that the center evaluation value CR is equal to or lower than the center threshold CRth and that the periphery evaluation value PR is equal to or lower than the periphery threshold PRth (Yes in S98 and Yes in S100), the test controller 14 determines that the examinee has a normal level of attention ability (S104). In a case where the respective comparisons show that the center evaluation value CR exceeds the center threshold CRth and that the periphery evaluation value PR exceeds the periphery threshold PRth (No in S98 and No in S102), the test controller 14 determines that the level of attention ability of the examinee is low and thus abnormal (S108). In a case where the respective comparisons show CR>CRth and PR<=PRth (No in S98 and Yes in S102) or CR<=CRth and PR>PRth (Yes in S98 and No in S100), the test controller 14 determines the need for a retest as it is difficult to accurately judge the attention ability of the examinee, based on the result of the last test (S106).

As is obvious from the above-described description, the evaluation value CR of a plurality of center reaction times C[i] and the evaluation value PR of a plurality of periphery reaction times P[i] are obtained in this example, and it is determined that the attention ability of the examinee is normal only in a case where the evaluation values CR, PR are both equal to or larger than the respective predetermined thresholds CRth, PRth. In other words, as the center reaction time C[i] and the periphery reaction time P[i] are independently evaluated in this example, it is possible to individually evaluate the attention ability in the central vision and that in a peripheral vision.

Further, the respective sums of the respective medians Cmed, Pmed of the reaction time and the respective excessive sample variations Crms, Prms are used as the evaluation values CR, PR of the respective reaction times in this example. This structure enables a more accurate detection of a problem in an attention ability due to drinking. That is, although a mere glance at the representative value (a median or an average) of the reaction times can give an idea of an approximate level of attention ability, it is difficult to make a clear determination as to whether or not there has been drinking of alcohol with only a glance at the representative value of the reaction times, since even a drinker examinee can demonstrate a high attention ability over a short period of time.

The attention ability of a drinker, however, tends to drop sharply as time passes or in response to a subtle disturbance (for example, noise). Thus, a drinker may not maintain a high attention ability. In view of the above, the reaction times for tasks undertaken by drinker examinees tend to vary so as to spread largely in an unfavorable direction, compared with that of not-drinker examinees. The excessive sample variations Crms, Prms are parameters indicating the magnitude of such a variation toward the unfavorable direction. Use of the evaluation values CR, PR reflecting such excessive sample parameters Crms, Prms enables a more accurate detection of a problem in attention ability due to drinking.

Note that the above-described procedure for evaluation is a mere example and an attention ability can be evaluated in an arbitrarily modified manner, provided that the evaluation is made based on the center reaction time C[i] and the periphery reaction time P[i]. For example, although the center evaluation value CR is obtained as CR=Cmed+Crms and the periphery evaluation value PR is obtained as PR=Pmed+Prms in the above example, these expressions for calculation of the evaluation values can be arbitrarily modified. For example, a representative value (for example, an average or a median) of a plurality of center reaction times C[i] may be used as an evaluation value of the center reaction time C[i]. Similarly, a representative value of a plurality of periphery reaction times P[i] may be used as an evaluation value of the periphery reaction time P[i].

Although a retest is determined without evaluation of the center reaction time C[i] and the periphery reaction time P[i] in the case where the memorizing evaluation value MR is less than the memorizing threshold MRth in the above-described example, the memorizing evaluation value MR may not be compared with the memorizing threshold MRth, and instead a coefficient in accordance with the memorizing evaluation value MR may be used in calculation of a center evaluation value CR and a periphery evaluation value PR. For example, a coefficient Km=1−MR may be obtained to calculate the evaluation value CR of the center reaction time C[i] as CR=(Cmed+Crms)+Km and the evaluation value PR of the periphery reaction time P[i] as PR=(Pmed+Prms)+Km. With this structure, a lower percentage of correct answers relative to the memorizing tasks leads to higher center evaluation value CR and periphery evaluation value PR (that is, a worse evaluation).

Although a memorizing task is executed in parallel with a center task or a periphery task in the above description, a memorizing task is omissible. That is, step S28 in FIGS. 8 and S80 in FIG. 13 are omissible.

Although an examinee operating a switch not correlated to a task being executed is not reflected in the evaluation in the above example, it may be arranged such that an examinee operating a switch not correlated to a task executed, that is, a so-called "erroneous answer", worsens the evaluation of the attention ability. For example, in a case where a switch not correlated to the center task is operated while a center task is being executed, the center reaction time C[i] for that center task may be considered as a maximum permissible time.

In a case where an examinee executes a memorizing reaction operation to react to a memorizing task, the examinee may not be able to smoothly execute a center reaction operation or a periphery reaction operation during a predetermined period preceding or following the memorizing reaction operation that is executed. Thus, if the performance in a center task or a periphery task generated during such a corresponding period is taken into consideration for evaluation, the attention ability of the examinee cannot be accurately determined. To address the above, in a case where the target image 50 is displayed as the memorizing task image 52, performance in a center task or a periphery task generated within a predetermined period of time after the display of the target image 50 may be excluded from evaluation.

As described above, the attention ability test device 10 in this example generates a center task in the central area 30 of the display area 13 and a periphery task in the peripheral area 34 at random. This structure enables appropriate testing of the attention ability in the central vision of an examinee and that in a peripheral vision. Further, a center task and a periphery task are both a "changing task" in which the central image 40 and the peripheral image 42 respectively change in this example. With a "changing task" it is more difficult to find a change, compared with an "appearing task" in which a peripheral image 42 appears, as described above. Setting a center task and a periphery task as a "changing task" can ensure an appropriate level of difficulty of a periphery task even when the display area 13 is small in dimension, that is, when the peripheral image 42 cannot be displayed at a position sufficiently separated from the central image 40. This enables appropriate testing of the attention ability of an examinee. Further, a structure in this example, in which a plurality of peripheral images 42 are displayed and any one peripheral image 42 among the plurality of peripheral images 42 is changed in a periphery task, can further enhance the level of difficulty of the periphery task. This enables appropriate testing of the attention ability of an examinee even when the peripheral image 42 cannot be displayed at a position sufficiently separated from the central image 40.

Use of the attention ability test device 10 disclosed in this specification can effectively prevent drunk driving at low cost. Note here that a large number of drinking detection devices for detecting drinker drivers have been conventionally suggested. Most of such devices, however, are devices for inspecting exhalation of drivers or examining the countenance of the faces of drivers, and thus require devices not originally equipped in the vehicles, such as an exhalation collecting device, an alcohol sensor, a camera for capturing images of the faces of drivers, or the like. Thus, such conventional drinking detection devices need high introduction costs. In contract, the attention ability test device 10 in this example can use an extant display 12 and input device 20, originally equipped in the vehicle 100, and thus can reduce the introduction cost.

Note that the above-described structures are mere examples, and structures can be arbitrarily modified provided that the structural elements defined in claim 1 are included. For example, although the above-described attention ability test device 10 is mounted in a vehicle 100 mainly to prevent drunk driving, the attention ability test device 10 may be mounted outside a vehicle to detect any state other than a drinking state. For example, the attention ability test device 10 is usable when newly granting or updating a driver's license to test the attention ability of a licensee. Further, the attention ability test device 10 in this example may be installed in medical facilities to inspect the influence of medicines (for example, antidepressants) that act on diseases (for example, glaucoma or dementia) or mental condition of patients, on the attention ability of the patients.

Although the display area 13 is described as a continuous area in the above-described example, the display area 13 may be composed of two or more sections. Specifically, for example, two or more displays (for example, the display of a smart phone) may be used to constitute the display area 13, with one installed so as to cover the central area 30 and the other to cover the peripheral area 34.

REFERENCE SIGNS LIST

10 attention ability test device, 12 display, 13 display area, 14 test controller, 16 processor, 18 memory, 20 input device, 21 communication I/F, 22 steering switch, 30 central area, 32 intermediate area, 34 peripheral area, 40 central image, 41, 43 route image, 42 peripheral image, 50 target image, 52 memorizing task image, 100 vehicle, 10 instrument panel, 110 steering wheel, 120 vehicle controller, 200 information terminal.

The invention claimed is:

1. An attention ability test device, comprising:
a display having a display area;
an input device for receiving an operation performed by an examinee; and
a test controller,
wherein
the test controller generates at random at least one of a center task and a periphery task while displaying a central image in a central area of the display area, and displaying one or more peripheral images in a peripheral area of the display area, the center task being a task of changing the central image such that a first shape moves around a first circular path at a first constant speed while expanding in size at a second constant speed, the periphery task being a task of changing the peripheral image such that a second shape moves around a second circular path at a third constant speed while expanding at a fourth constant speed, measures, as a reaction time, a period of time from generation of the center task or the periphery task to execution of a predetermined operation by the examinee having recognized the generation, and evaluates a state of an attention ability of the examinee, based on the reaction time.

2. The attention ability test device according to claim 1, wherein the test controller displays a plurality of the peripheral images in the peripheral area, and executes the periphery task of changing one peripheral image selected at random from among the plurality of peripheral images.

3. The attention ability test device according to claim 1, wherein
the test controller generates the center task and the periphery task at a plurality of times in a single flow of processing for a test to obtain a plurality of center reaction times and a plurality of periphery reaction times, the center reaction time being a reaction time relative to the center task, the periphery reaction time being a reaction time relative to the periphery task, and
the test controller calculates a center evaluation value indicating an attention ability of the examinee in a central vision, based on the plurality of center reaction times, and a periphery evaluation value indicating an attention ability of the examinee in a peripheral vision, based on the plurality of periphery reaction times.

4. The attention ability test device according to claim 3, wherein
the center evaluation value is a sum of a representative value of the plurality of center reaction times and an excessive sample variation of the center reaction time,
the periphery evaluation value is a sum of a representative value of the plurality of periphery reaction times and an excessive sample variation of the periphery reaction time, and
the excessive sample variation is a root mean square of a deviation between the representative value and one or more excessive samples among the plurality of reaction times, the excessive samples being reaction times larger than the representative value.

5. The attention ability test device according to claim 1, wherein
the test controller generates a memorizing task in the central area of the display area in parallel with the center task or the periphery task,
the memorizing task is to present a target image as a memorizing target to the examinee, and then to sequentially display a plurality of candidate images, including the target image, in a random order as memorizing task images in the central area, and
the test controller counts, as a number of correct answers, a number of times the examinee, having recognized display of the target image as the memorizing task image in the central area, executes the predetermined operation within a predetermined permissible time after the display.

6. The attention ability test device according to claim 5, wherein
the test controller calculates an evaluation value of the memorizing task, based on the number of correct answers, and
the test controller determines a need of a retest in a case where the evaluation value of the memorizing task is less than a predetermined memorizing threshold.

7. The attention ability test device according to claim 1, wherein the display is a vehicle-mounted display that is mounted in a position where the display area is visually recognizable from a driver's seat, and the input device includes one or more steering switches equipped on a steering wheel of a vehicle.

8. A vehicle, comprising:

the attention ability test device according to claim 1, and a vehicle controller for controlling behavior of the vehicle, wherein the vehicle controller changes the behavior of the vehicle, based on a result of evaluation outputted from the attention ability test device.

9. The attention ability test device according to claim 5, wherein:

the test controller displays the memorizing task images inside the first circular path.

10. An attention ability test method, comprising the steps of:

generating at random at least one of a center task and a periphery task while displaying a central image in a central area of a display area of a display, and displaying one or more peripheral images in a peripheral area of the display area, the center task being a task of changing the central image such that a first shape moves around a first circular path at a first constant speed while expanding in size at a second constant speed, the periphery task being a task of changing the peripheral image such that a second shape moves around a second circular path at a third constant speed while expanding at a fourth constant speed, measuring, as a reaction time, a period of time from generation of the center task or the periphery task to execution of a predetermined operation by an examinee having recognized the generation, and evaluating a state of an attention ability of the examinee, based on the reaction time.

* * * * *